United States Patent
Foster et al.

(10) Patent No.: US 11,147,926 B2
(45) Date of Patent: *Oct. 19, 2021

(54) INTRATHECAL BACLOFEN PHARMACEUTICAL DOSAGE FORMS AND RELATED DELIVERY SYSTEM

(71) Applicant: PIRAMAL CRITICAL CARE, INC., Bethlehem, PA (US)

(72) Inventors: John J. Foster, Stillwater, MN (US); Thomas R. Prentice, Lake Elmo, MN (US)

(73) Assignee: PIRAMAL CRITICAL CARE, INC., Bethlehem, PA (US)

(*) Notice: Subject to any disclaimer, the term of this patent is extended or adjusted under 35 U.S.C. 154(b) by 52 days.

This patent is subject to a terminal disclaimer.

(21) Appl. No.: 15/014,893

(22) Filed: Feb. 3, 2016

(65) Prior Publication Data

US 2016/0151575 A1    Jun. 2, 2016

Related U.S. Application Data

(63) Continuation of application No. 14/725,714, filed on May 29, 2015, now abandoned, which is a continuation-in-part of application No. 12/403,190, filed on Mar. 12, 2009, now abandoned, and a continuation-in-part of application No. 14/574,733, filed on Dec. 18, 2014, now Pat. No. 9,474,732, which is a continuation of application No. 12/701,342, filed on Feb. 5, 2010, now Pat. No. 8,969,414.

(60) Provisional application No. 61/037,544, filed on Mar. 18, 2008, provisional application No. 61/150,337, filed on Feb. 6, 2009.

(51) Int. Cl.
| | |
|---|---|
| *A61M 5/315* | (2006.01) |
| *A61M 5/31* | (2006.01) |
| *A61K 31/197* | (2006.01) |
| *A61K 47/02* | (2006.01) |
| *A61K 9/00* | (2006.01) |

(52) U.S. Cl.
CPC ....... *A61M 5/31535* (2013.01); *A61K 9/0019* (2013.01); *A61K 9/0085* (2013.01); *A61K 31/197* (2013.01); *A61K 47/02* (2013.01); *A61M 5/31* (2013.01); *A61M 5/315* (2013.01); *A61M 2005/3114* (2013.01); *A61M 2005/3125* (2013.01); *A61M 2205/6009* (2013.01); *A61M 2205/6081* (2013.01)

(58) Field of Classification Search
None
See application file for complete search history.

(56) References Cited

U.S. PATENT DOCUMENTS

| | | |
|---|---|---|
| 5,149,713 A | 9/1992 | Bousquet |
| 5,256,154 A | 10/1993 | Liebert |
| 5,980,927 A | 11/1999 | Nelson |
| 6,380,176 B2 | 4/2002 | Takahashi |
| 6,629,954 B1 | 10/2003 | Heruth |
| 6,754,536 B2 | 6/2004 | Swoyer |
| 6,969,383 B2 | 11/2005 | Trissel |
| 7,824,697 B2 | 11/2010 | Trissel |
| 7,998,120 B2 | 8/2011 | Sano |
| 8,062,647 B2 | 11/2011 | Trissel |
| 8,083,722 B2 | 12/2011 | McKay |
| 8,357,379 B2 | 1/2013 | Trissel |
| 8,529,916 B2 | 9/2013 | Trissel |
| 8,969,414 B2 | 3/2015 | Foster |
| 2001/0051618 A1 | 12/2001 | Takahashi |
| 2004/0062819 A1 | 4/2004 | Hildebrand |
| 2004/0220545 A1 | 11/2004 | Heruth |
| 2004/0267194 A1 | 12/2004 | Sano |
| 2005/0004219 A1 | 1/2005 | Hildebrand |
| 2005/0090554 A1 | 4/2005 | Devane |
| 2005/0244503 A1 | 11/2005 | Rabinow |
| 2006/0009523 A1* | 1/2006 | Trissei ............... A61K 31/195 514/561 |
| 2006/0084925 A1* | 4/2006 | Ramsahoye ....... A61M 5/31511 604/189 |
| 2006/0142396 A1 | 6/2006 | Meythaler |
| 2010/0056989 A1 | 3/2010 | McKay |
| 2010/0106097 A1 | 4/2010 | Elmouelhi |
| 2011/0269836 A1 | 11/2011 | Foster |
| 2013/0331451 A1 | 12/2013 | Trissel |
| 2015/0105466 A1 | 4/2015 | Foster |
| 2015/0258279 A1 | 9/2015 | Foster |
| 2016/0151575 A1 | 6/2016 | Foster |

FOREIGN PATENT DOCUMENTS

| | | |
|---|---|---|
| EP | 2548594 A1 | 1/2013 |
| JP | 63-253022 | 10/1988 |
| WO | 2002085428 | 10/2002 |

(Continued)

OTHER PUBLICATIONS

Syringe Labelling in critical care areas article (2003).*
Boca et al. (Pharmaceutical Technology (Sep. 2002), pp. 62-70).*
Colas et al. ("Silicones in Pharmaceutical Applications" (2006)).*
Sigg, Solubility and Stability of Intrathecal Baclofen Solutions at High Concentrations: Implications for Chronic Use in the SynchroMed Infusion System, White Paper, 2007, Medtronic Neurological, 8 pgs.
International Search Report and Written Opinion dated Oct. 4, 2010 from related International application No. PCT/US2010/000352, 7 pgs.

(Continued)

*Primary Examiner* — Patricia Duffy
*Assistant Examiner* — Garen Gotfredson
(74) *Attorney, Agent, or Firm* — Merchant & Gould P.C.

(57) ABSTRACT

According to the subject invention, there is disclosed, a dosage and packaging configuration which includes the use of color-coded pre-filled syringes and vials to fill and refill infusion systems with existing and new dosage forms of intrathecal baclofen.

5 Claims, 2 Drawing Sheets

(56) References Cited

FOREIGN PATENT DOCUMENTS

| WO | 2006017235 | 2/2006 |
|---|---|---|
| WO | 2010090765 A3 | 8/2010 |

OTHER PUBLICATIONS

Godwin, Stability of a Baclofen and Clonidine Hydrochloride Admixture for Intrathecal Administration, Hospital Pharmacy, 2001, vol. 36, No. 9, pp. 950-954.
Sitaram, Stability and compatibility of intrathecal admixtures containing baclofen and high concentrations of morphine, Int. J. Pharm., Jul. 1, 1997, vol. 153, Issue 1, pp. 13-24.
Cutrignelli, Comparative effects of some hydrophilic excipients on the rate of gabapentin and baclofen lactamization in lyophilized formulations, Int. J. Pharm., Mar. 2007, vol. 332, Issue 1-2, pp. 98-106.
Center for Drug Evaluation and Research, Guidance for Industry and Review Staff, Nonclinical Safety Evaluation of Reformulated Drug Products and Products Intended for Administration by an Alternate Route, Pharmacology/Toxicology, Mar. 2008, pp. 1-8.
U.S. Pharmacopeia <161> Transfusion and Infusion assemblies and Similar Medical Devices, available at http://www.pharmacopeia.cn/v29240/usp29nf24s)_c161.html; downloaded Apr. 18, 2014, 2 pgs.
Orange Book entry for Lioresal. Accessed at <http://www.accessdata.fda.gov/scripts/cder/ob/docs/obdetail.cfm?Appln_No=022462&TABLE1=OB_Rx> downloaded Jul. 29, 2011, 2 pgs.
About Gablofen Common Questions Accessed at <http://www.gablofen.com/common-questions.pho> downloaded Jul. 29, 2011, 3 pgs.
Baclofen; AHFS Drug Information 2003, Baclofen, 1314-1318.
Allen, Stability of baclofen, captopril, dilitiazem hydrochloride, dipyridamole, and flecainide acetate in extemporaneously compounded oral liquids, American Journal of Health System Pharmacy, 1996, 53, 2179-84.
Cruaud, The characterization and release kinetics evaluation of baclofen microspheres designed for intrathecal injection, International Journal of Pharmaceutics, 1999, 177, 274-257.
Johnson, Stability of an extemporaneously compounded baclofen oral liquid, American Journal of hospital Pharmacy, 1993, 50, 2353-5.
Lioresal Package Insert; Medtronic, Inc., 2003, 2 pgs.
Medtronic Bar Code; Medtronic, Inc., Use by Date 04/070/2010, 1 pg.
Medtronic Instructions for Use; Medtronic, Inc., 2003, 20 pgs.
Medtronic Labels; Medtronic, Inc., Use by Date Mar. 31, 2011, 5 pgs.
Medtronic Product Pics; Medtronic, Inc., pp. 528-548.
Seed, Silanizing Glassware, Current Protocols in Immunology, 1997, Supplement 21, Appendix 3K Basic Protocol, 2 pgs.
Non-final Office action from U.S. Appl. No. 12/403,190 dated Aug. 9, 2011, 11 pgs.
Final Office action from U.S. Appl. No. 12/403,190 dated Apr. 23, 2011, 11 pgs.
Non-final Office action from U.S. Appl. No. 12/403,190 dated May 17, 2013, 10 pgs.
Final Office action from U.S. Appl. No. 12/403,190 dated Jan. 22, 2014, 11 pgs.
Non-final Office action from U.S. Appl. No. 12/403,190 dated Oct. 8, 2014, 13 pgs.
Holloway, "Systemic Pharmacomodulation of Transient Lower Esophageal Sphincter Relations," Amer. J. Medicine, 2001, vol. 111(8A), pp. 178S-185S.
Baum, "Production and Testing of Baclofen Solutions," Pharmazeutische Zeitung, 1988, vol. 133, pp. 2832, Germany (English Abstract).
Ridley, "Intrathecal Baclofen Therapy: Ten Steps Towerd Best Practice," Journal of Neuroscience Nursing, 2006, 38:2, pp. 72-82.
Cardiff, "Concentrating on Baclofen," Australian Journal of Hospital Pharmacy, Feb. 1995, vol. 25, No. 1, pp. 102-103 (abstract).
U.S. Department of Health and Human Services Food and Drug Administration, "Guidance for Industry: Container Closure Systems for Packaging Human Drugs and Biologics", May 1999, pp. 23-25.
Moberg-Wolf, "Potential clinical impact of compounded versus noncompounded intrathecal baclofen," Archives of Physical Medicine and Rehabilitation, Nov. 2009, vol. 90, Issue 11, pp. 1815-1820.
Ahuja, "Baclofen," Analytical Profiles of Drug Substances, 1985, vol. 14, pp. 527-548.
Gupta, "Quantiation of 4-(4-chlorophenyl)-2-Pyrrolidine in vaclofen powder and tablets," Drug Develop. Indust. Pharm., 1988 vol. 14, pp. 1623-1628.
Final Office action from U.S. Appl. No. 12/403,190 dated Mar. 6, 2015, 13 pgs.
Office action from EP Application 11006015.9 dated Aug. 7, 2015, 3 pgs.
Partial European Search Report from EP Application 11006015.9 dated Mar. 16, 2012, 5 pgs.
European Search Report from EP Application 11006015.9 dated Jul. 3, 2012, 5 pgs.
Non-final Office action from U.S. Appl. No. 14/574,733 dated Feb. 1, 2016, 13 pgs.
Health Canada, "Process Validation: Moist Heat Sterilization for Pharmaceuticals," 2002, pp. 1-15 of 15, downloaded on Jan. 10, 2016 from www.hc-sc.gc.ca/dhp-mps/compli-conform/gmp-bpf/validation/mhsp-schpp-eng.php.
Medtronic, "Lioresal(R) Intrathecal" (baclofen injection) product information, Medtronic, Inc., Aug. 2007, downloaded from "www.pdr3d.com" on Sep. 5, 2012, pp. 1-14 of 14.
Declaration of Thomas R. Prentice Under 37 C.F.R. 1.132, filed in parent U.S. Appl. No. 12/701,342 on Mar. 15, 2013, 3 pages.
Notice of Allowance from U.S. Appl. No. 14/574,733 dated Jun. 29, 2016, 17 pgs.
Notice of Allowance from U.S. Appl. No. 12/701,342 dated Sep. 24, 2014, 10 pgs.
Declaration of Brian D. Doty Under 37 C.F.R. 1.132, filed in parent U.S. Appl. No. 12/701,342 on Feb. 6, 2015, 4 pgs.
5.8 Methods of Sterilization, The International Pharmacopoeia, Fifth Edition, 2015, 3 pgs.
Non-final Office action from U.S. Appl. No. 14/725,714 dated Jul. 1, 2016, 20 pgs.
Boca, "An Overview of the Validation Approach for Moist Heat Sterilization, Part I," Pharmaceutical Technology, Sep. 2002, pp. 62-70.

* cited by examiner

INTRATHECAL BACLOFEN PHARMACEUTICAL DOSAGE FORMS AND RELATED DELIVERY SYSTEM

This application is a continuation of U.S. patent application Ser. No. 14/725,714, filed May 29, 2015, which is a continuation-in-part application of U.S. patent application Ser. No. 12/403,190, filed Mar. 12, 2009, which claims the benefit of priority of U.S. Provisional Application No. 61/037,544, filed Mar. 18, 2008, and also is a continuation-in-part application of U.S. patent application Ser. No. 14/574,733, filed Dec. 18, 2014, which is a continuation of U.S. patent application Ser. No. 12/701,342 (now Pat. 8/969,414), filed Feb. 5, 2010, which claims the benefit of priority of U.S. Provisional Application No. 61/150,337, filed Feb. 6, 2009, the disclosures of which are hereby incorporated by reference in their entireties.

The present invention relates generally to a syringe vial or vial that is filled in advance with a liquid to be injected. More specifically, the present invention is directed to pre-filled syringes and vials to fill and refill infusion systems with existing and new forms of intrathecal baclofen.

Baclofen is a skeletal muscle relaxant and antispastic agent. Baclofen is a structural analog of the inhibitory neurotransmitter gamma-aminobutyric acid (GABA), and may exert its effects by stimulation of the $GABA_B$ receptor subtype. Baclofen is the generic (USAN) name (USP Dictionary of USAN and International Drug Names 2003) for 4-amino-3-(p-chlorophenyl)butyric acid, a derivative of γ-aminobutyric acid. Its structural formula is:

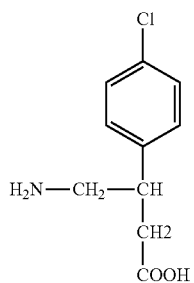

Baclofen is a white to off-white, odorless or practically odorless crystalline powder, with a molecular weight of 213.66 g/mol. It is slightly soluble in water, very slightly soluble in methanol, and insoluble in chloroform. Baclofen can be administered orally, but when injected directly into the intrathecal space of a patient effective cerebrospinal fluid (CSF) concentrations are achieved with resultant plasma concentrations 100 times less than those occurring with oral administrations.

As indicated in US patent application 2006/0009523, which is hereby incorporated by reference, baclofen solutions having concentrations in the range of about 3 to about 8 mg/mL can be obtained by mixing the appropriate quantity of baclofen with an aqueous diluent and heating the solution to a temperature of at least about 30° C., at least about 40° C., at least about 50° C., preferably at least about 60° C., and most preferably at least about 70° C. and a temperature of less than about 90° C., less than about 95° C., less than about 100° C., less than about 121° C., or most preferably less than the temperature at which baclofen thermal degrades to a significant degree. The heat is applied while simultaneously subjecting the solution to intense agitation, e.g. sonication, high-speed stirring, etc. The temperature range of at least about 60° C. to at less than about 100° C. is most preferred. Further, it is generally preferable, although not required, that the aqueous solution be heated to a temperature lower than its boiling point to prevent significant evaporation of the aqueous solvent during dissolution. Dissolution temperatures of 100° C. or higher that do not boil off the aqueous solvent can be obtained by means known to those of skill in the art, such as by increasing the atmospheric pressure that the solution is subjected to during heating. One common means of achieving this result is by autoclaving the solution.

Stable baclofen solutions can be produced by acidification and back titration. Baclofen solutions having concentrations up to about 10.0 mg/mL can be prepared by dissolving baclofen in an acidic solution, preferably one having a pH lower than the $pKa_1$ of baclofen. For example, pH values lower than about 3.87, lower than about 3.0, lower than about 2.0, lower than about 1.5, or even lower than a pH of about 1.0 can be used advantageously. Surprisingly, once the baclofen has been dissolved in the acidic solution, and prior to pharmaceutical administration, the baclofen solution can be back titrated to a pH of 4.0 to 8.5 without precipitation of baclofen particulates. The titration is carried out by adding a base to the acidic solution until the pH is adjusted to a pH in the desired range. A final pH of 5.0 to 7.0 is currently preferred for baclofen solutions intended for pharmaceutical uses such as intrathecal injection, but pH ranges of 4.5 to 8.0 and of 4.0 to 8.5 can also be suitable for such uses. These pH ranges are intended to be illustrative of appropriate values for uses such as intrathecal injection. The appropriate pH ranges for any particular pharmaceutical application will be readily apparent to those skilled in the art, and the final pH of the baclofen solution can be any pharmaceutically acceptable pH appropriate for a given use. In addition, baclofen solutions prepared by this method can be stored at a pH that is not appropriate for a given pharmaceutical use so long as the solution is titrated to a pharmaceutically acceptable pH prior to administration.

Alternately, stable baclofen solutions can be produced by alkalinization and back titration. That is, solutions having concentrations of baclofen of about 10.0 mg/mL or lower can be prepared by dissolving baclofen in a basic solution, preferably one having a pH higher than the $pKa_2$ of baclofen. For example, solutions of pH higher than about 9.62, higher than about 10.0, higher than about 11.0, higher than about 12.0, and even higher than the pH of about 13.0 can be used advantageously. Once the baclofen is dissolved in the basic solution the pH can be back titrated to a pH of about 4.0 to 8.5, or preferably can be titrated to a pH of 5.0 to 7.0, or to other pH values appropriate for pharmaceutical uses such as intrathecal injection, as discussed above. For use in other applications, pharmaceutical or otherwise, or during storage prior to use the baclofen solution can be titrated to a lower pH or can be maintained for some period of time at the original basic pH.

Presently, intrathecal baclofen is stored in ampoules. Typical procedure for filling infusion systems includes breaking the ampoules to open them, removing the drug from the ampoule and filtering it using a syringe with an in-line filter and needle, removing the needle from the syringe and replacing it with a catheter that includes a second in-line filter and needle. The needle is then inserted through the skin into the implanted pump reservoir and the fluid is dispensed and filtered, filling the infusion system reservoir with the drug. This process may need to be done from 1 to 4 times for a single filling, depending on the reservoir size and the ampoule configuration selected. There are multiple issues with the current process and the need to enhance safety with intrathecal drugs is paramount.

As used herein, the terms below have the meanings indicated.

The term "pre-filled," as used herein, means containing an exact, pre-determined dose of a sterile pharmaceutical composition.

The present invention implements a pre-filled syringe that is ready for immediate delivery to the infusion system. The packaging system includes a syringe with a leur-lock tip filled with intrathecal baclofen, a color coding system (label) for the various concentrations of the drug product and size of syringe, a package, a label, and instructions for use.

Since the drug in the syringe is already prepared, the process of drawing up and filtering the drug into a syringe prior to refilling the infusion system is eliminated. Eliminating this process makes filling and refilling the infusion system safer and easier. The pre-filled syringe is easier to use because the practitioner does not have to draw up and filter the drug while administering the therapy to the patient. The syringe's label or plunger is color coded by concentration and syringe sizes, thereby reducing practitioner error and increasing safety to the recipient. Higher concentration formulations will be available to reduce the number of times the recipient must be injected with the needle. The pre-filled syringe also eliminates the potential of contamination of the drug with glass particles from the ampoule, bacteria and the like.

Further features and advantages of the invention, as well as the structure and operation of various embodiments of the invention, are described in detail below.

Figure 1:
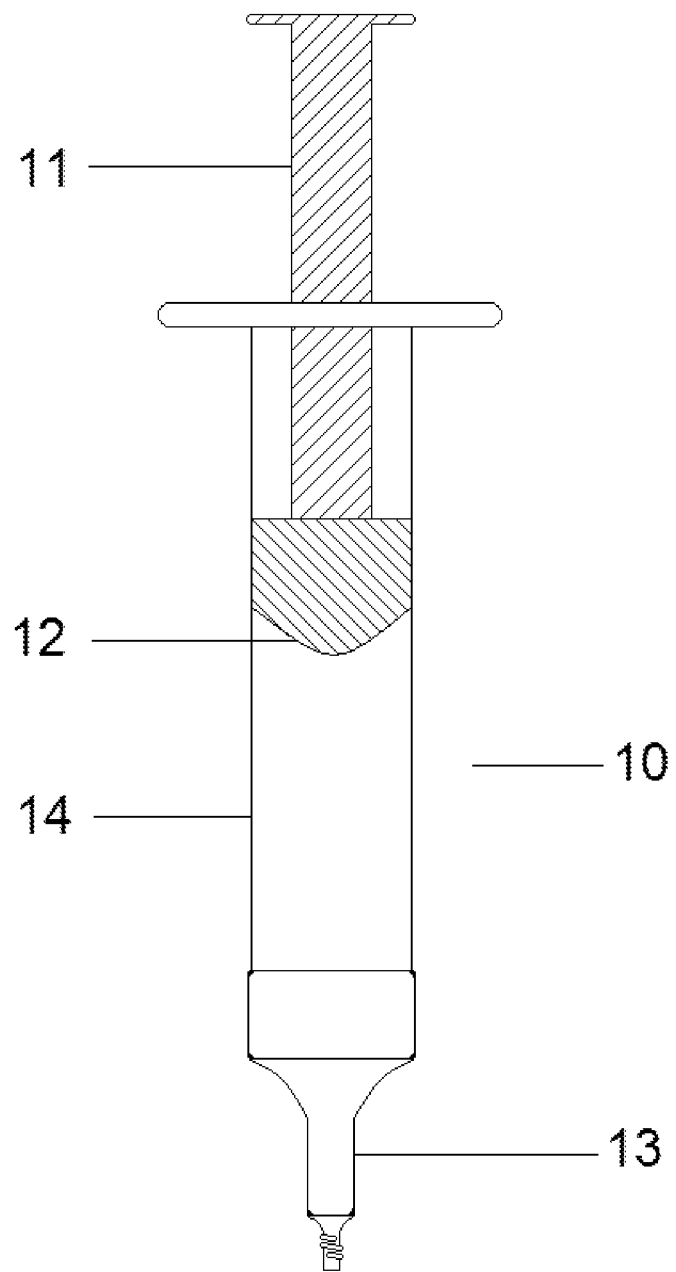
FIG. 1 is an illustration of the pre-filled syringe according to an exemplary embodiment.

The barrel 14 is made of glass or plastic having two open ends. The pre-filled syringe 10 can have sizes of 5 milliliters, 20 milliliters, or 40 milliliters. One end of the barrel 14 is closed off by a plunger 11 that forces the medical liquid (not shown) to the other end of the barrel 14 when dispensing. A gasket 12 is attached to the plunger 11 for sealing the medical liquid in the barrel 14. The gasket 12 is made of a rubbery elastic material, such as natural rubber or synthetic rubber. The dispensing end of the barrel 14 is closed off by a leur-lock tip 13. The leur-lock tip 13 mates with the infusion system for dispensing the medical liquid.

The pre-filled syringe 10 is filled with a medical fluid, in particular, intrathecal baclofen. The solution comprises baclofen USP, Sodium Chloride, and water and is approved by the Food and Drug Administration. The solution is formed aseptically, is terminally sterilized as described below, and inserted into sterilized syringes. The dosages of intrathecal baclofen are 2.5 milligrams per 5 milliliters, 40 milligrams per 20 milliliters, 80 milligrams per 40 milliliters, 80 milligrams in 20 milliliters, or 160 milligrams in 40 milliliters. The available high concentrations and large syringe sizes eliminate the need for multiple operations to fill the pump reservoir, thus reducing the potential of practitioner error and thereby increasing the safety of the recipient. Further, the syringes have minimal head space, which leads to a decrease in degradation of the baclofen solution via oxidation. The label or plunger 11 of each pre-filled syringe 10 has a distinct color for identifying the dosages. The color-coded system further helps to eliminate practitioner error of injecting the wrong dose. The product is packaged, labeled, and sterilized.

Figure 2:
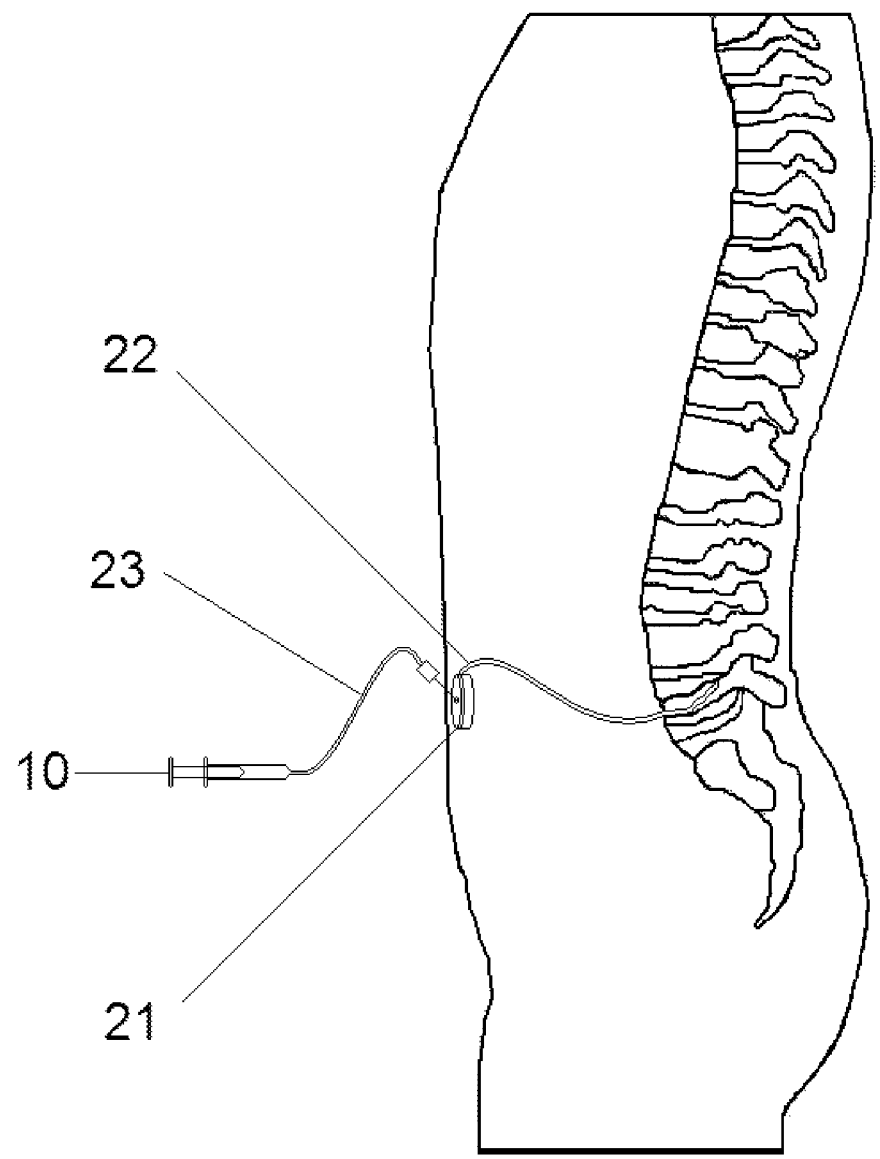
FIG. 2 is an illustration of the pre-filled syringe as used with an infusion system.

FIG. 2 displays the pre-filled syringe 10 as used with the pump system. Pump refill kits are commercially available from Medtronic® and include a catheter 23 for connecting the pre-filled syringe to the pump 21. Intrathecal baclofen may be dispensed from the pre-filled syringe 10, through the catheter 23, into the pump 21 without the baclofen being drawn and filtered. The pump 21 then pumps the intrathecal baclofen through a second catheter 22 to a desired location in the body. The pre-filled syringe can be used with the Medtronic SynchroMed Infusion System®, the Johnson and Johnson Codman® division pumps, and InSet® technologies pumps.

In an alternative embodiment, the baclofen may be stored in a vial. The vial can be made of glass or plastic. It may be closed off at the top by a stopper with crimp top. Flip off tops may be used for tamper proof and color coding. Color coding is done by concentration and syringe sizes, thereby reducing practitioner error and increasing safety to the recipient. Types of stopper that may be used include rubber and plastic. The size of the vial may be 20 milliliters or 40 milliliters. In the 20 milliliter vial, the concentration of intrathecal baclofen may be 500 micrograms per milliliter, 2000 micrograms per milliliter, or 4000 micrograms per milliliter. In the 40 milliliter vial, the concentration of baclofen may be 2000 micrograms per milliliter or 4000 micrograms per milliliter.

The baclofen solution is aseptically inserted into vials and the vials are terminally sterilized. Common sterilization protocols call for heating the solution to 121.1° C. with a sterilization time ($F_0$) of about 30 minutes. Baclofen, however, is heat-sensitive and forms a poorly soluble degradation product, 4-(4-chlorpheyl)-2-pryyolidone (4-CPP), upon exposure to heat. For example, baclofen solutions sterilized by moist heat contain up to 1A wt % of 4-CPP, which is higher than the permissible level for the marketed product (Sigg et al., Solubility and Stability of Intrathecal Baclofen Solutions at High Concentrations: Implications for Chronic Use in the SynchroMed Infusion System, White Paper 2007, Minneapolis: Medtronic Neurological). Therefore, it is desirable to find and implement a sterilization method that utilizes less harsh conditions in order to prevent this thermal degradation from taking place, while continuing to meet sterility standards. Accordingly, vials containing baclofen solutions are steam heated at 121.1° C. for a $F_0$ of 7 minutes. Said terminally sterilized baclofen solutions contain less than 0.5 wt % of 4-CPP. The level of 4-CPP in said terminally sterilized baclofen solutions is less than that in previous formulations. For example, Lioresal Intrathecal (Medtronic) contains 0.6 wt % of 4-CPP.

Because the vials of baclofen solution are terminally sterilized, there is no need to filter the baclofen solution before use. This leads to an overall reduction in time needed to administer the baclofen solution versus the existing delivery methods which involve cracking open the ampoules and filtering the solution before administration to a patient in need, and additionally reduces the potential of practitioner error and thereby increases the safety of the recipient.

The method of processing the vials may cause baclofen to precipitate from solution or adsorb to the surface of the glass vial. Therefore, treating the glass vials with a coating intended to deactivate the reactivity of the glass surface may prevent this unwanted precipitation. This coating typically reacts with the hydroxyl groups of the glass and forms a more stable covalent bond. Silanization is one method of deactivating the glass surface, wherein the glass surface is reacted with silanes. The hydroxyl groups of the glass attack and displace the alkoxy groups on the silane thus forming a covalent —Si—O—Si— bond, rendering the glass surface inert.

In another embodiment, the vial described herein is coated with a compound that deactivates the glass surface, so possible reactions between baclofen and the glass are eliminated. Possible vials with this coating include vials treated with SCHOTT Type I plus® coating technology.

In a further embodiment, the vial described herein is silanized to prevent adsorption and precipitation of baclofen.

The presence of oxygen may lead to the oxidation of baclofen. In order to reduce the chances of oxidation of the baclofen solution while in vials, a blanket of nitrogen gas is laid across the vials before they are sealed to displace any oxygen present. Oxidation of the baclofen solution in syringes is minimized by the lack of head space in the syringes, which limits the presence of any gases, including oxygen, within the syringe.

In yet another embodiment, the baclofen solution is stored under a nitrogen atmosphere within the vial.

From the foregoing description, one skilled in the art can easily ascertain the essential characteristics of this invention, and without departing from the spirit and scope thereof, can make various changes and modifications of the invention to adapt it to various usages and conditions.

EXAMPLE 1

Preparation of 4.0 mg/mL Baclofen Solution

To 1 L of hot water was added 630.0 g sodium chloride, and the mixture was stirred for 10±2 minutes. To the resulting solution was added 280.0 g baclofen and 2 L hot water. The mixture was then stirred for 45 minutes. The resulting solution was diluted to 70 L with hot water and stirred for at least an additional 10 minutes.

EXAMPLE 2

Preparation of 2.0 mg/mL Baclofen Solution

To 1 L of hot water is added 315.0 g sodium chloride, and the mixture is stirred for 10±2 minutes. To the resulting solution is added 140.0 g baclofen and 2 L hot water. The mixture is then stirred for 45 minutes. The resulting solution is diluted to 70 L with hot water and stirred for at least an additional 10 minutes.

EXAMPLE 3

Preparation of 0.5 mg/mL Baclofen Solution

To 1 L of hot water was added 78.75 g sodium chloride, and the mixture was stirred for 10±2 minutes. To the resulting solution was added 35.0 g baclofen and 2 L hot water. The mixture was then stirred for 45 minutes. The resulting solution was diluted to 70 L with hot water and stirred for at least an additional 10 minutes.

EXAMPLE 4

Sterilization Protocol

A baclofen solutions described above were aseptically transferred to vials. The vials containing the solution were then steam-heated to 121.1° C. so that the $F_0$ for the resulting terminally sterilized solution was 7 minutes.

EXAMPLE 5

Percent 4-CPP Found in Baclofen Solutions

The percent of 4-CPP found in 0.5 mg/mL and 4.0 mg/mL baclofen solutions prepared as described above is presented in the table below.

| Baclofen solution | Percent (wt %) of 4-CPP |
| --- | --- |
| 0.5 mg/mL (#2118-101) | 0.346 |
| 0.5 mg/mL (#2118-102) | 0.436 |
| 0.5 mg/mL (#2118-103) | 0.39 |
| 4.0 mg/mL (#2133-101) | 0.377 |
| 4.0 mg/mL (#2133-102) | 0.415 |
| 4.0 mg/mL (#2137-101) | 0.442 |

What is claimed is:

1. A process for preparation of drug delivery system consisting of a packaged and labeled syringe pre-filled with a sterile solution of baclofen containing up to 0.5% by weight of (4-chlorophenyl)-2-pyrrolidone, for intrathecal delivery comprising the steps of:
   (i) adding sodium chloride solution to baclofen, wherein the baclofen is not filtered, to form a solution of baclofen having a concentration of 0.5 mg/ml, 2.0 mg/ml, or 3.0 mg/ml, wherein the pH of the baclofen solution is in the range of about 4.5 to about 8.0 or about 5.0 to about 7.0;
   (ii) sterilizing the solution of baclofen obtained in step (i) by steam heating at 121° C. so that the sterilization time ($F_0$) for the resulting terminally sterilized solution is 7 minutes;
   (iii) filling a syringe with 5 ml to 40 ml of the sterile solution of step (ii) and wherein the syringe has an internal surface treated to reduce reactivity of the internal surface;
   (iv) color coding a plunger and/or label of the syringe depending on the amount of said baclofen in said pre-filled syringe; and
   (v) closing a dispensing end of the syringe with a leur-lock tip, thereby forming the packaged and labeled pre-filled syringe.

2. The process of claim 1, wherein said color coding system is on said plunger.

3. The process of claim 1, wherein said color coding system is on the plunger and a label of said packaged and labeled pre-filled syringe.

4. The process of claim 3, wherein said color coding system is on a label of said packaged and labeled pre-filled syringe.

5. The process of claim 1, wherein said color coding system is also indicative of the amount of said baclofen in said pre-filled syringe.

* * * * *